United States Patent [19]

Gonser

[11] 4,062,099
[45] Dec. 13, 1977

[54] METHOD OF MAKING A SHIELD FOR A RADIATION PROJECTOR

[75] Inventor: Donald I. Gonser, Forest Park, Ohio

[73] Assignee: Dentsply Research and Development Corporation, Milford, Del.

[21] Appl. No.: 667,265

[22] Filed: Mar. 15, 1976

Related U.S. Application Data

[62] Division of Ser. No. 547,049, Feb. 4, 1975.

[51] Int. Cl.² .......................... B29C 27/00; B29F 5/00
[52] U.S. Cl. ........................................ 29/415; 29/447; 29/453; 264/1; 264/138; 264/159; 264/271; 264/294; 264/342 R; 264/334
[58] Field of Search ................ 264/230, 342 R, 271, 264/294, 138, 154, 146, 159, 334, 342, 1; 350/96 B, 96 R, 96 T, 96; 250/503, 504, 505, 519; 29/428, 415, 447, 453; 174/135; 240/1 LP

[56] References Cited

U.S. PATENT DOCUMENTS

| 1,435,311 | 11/1922 | Knight | 174/135 |
| 1,965,865 | 7/1934 | Thompson | 350/96 R |
| 2,042,536 | 6/1936 | Leguillon | 264/334 |
| 3,396,460 | 8/1968 | Wetmore | 264/230 |
| 3,499,210 | 3/1970 | Schellstede et al. | 29/447 |
| 3,614,415 | 10/1971 | Edelman | 240/1 LP |
| 3,641,332 | 2/1972 | Reick et al. | 240/1 LP |
| 3,894,731 | 7/1975 | Evans | 264/230 |

FOREIGN PATENT DOCUMENTS

| 661,868 | 11/1951 | United Kingdom | 264/159 |

*Primary Examiner*—Willard E. Hoag
*Attorney, Agent, or Firm*—James W. Pearce; Roy F. Schaeperlaus

[57] ABSTRACT

A shield for a radiation piping rod is formed by shrinking a length of plastic resin tubing on a rod or on a mandrel having a portion conforming to a portion of the rod to be shielded. The shrunken tubing is provided with a lengthened slit to permit stripping from the rod or mandrel to form the shield. The shield is mounted on the rod after stripping, and an air interface is formed between the rod and the shield to minimize loss of radiation caused by the shield.

4 Claims, 12 Drawing Figures

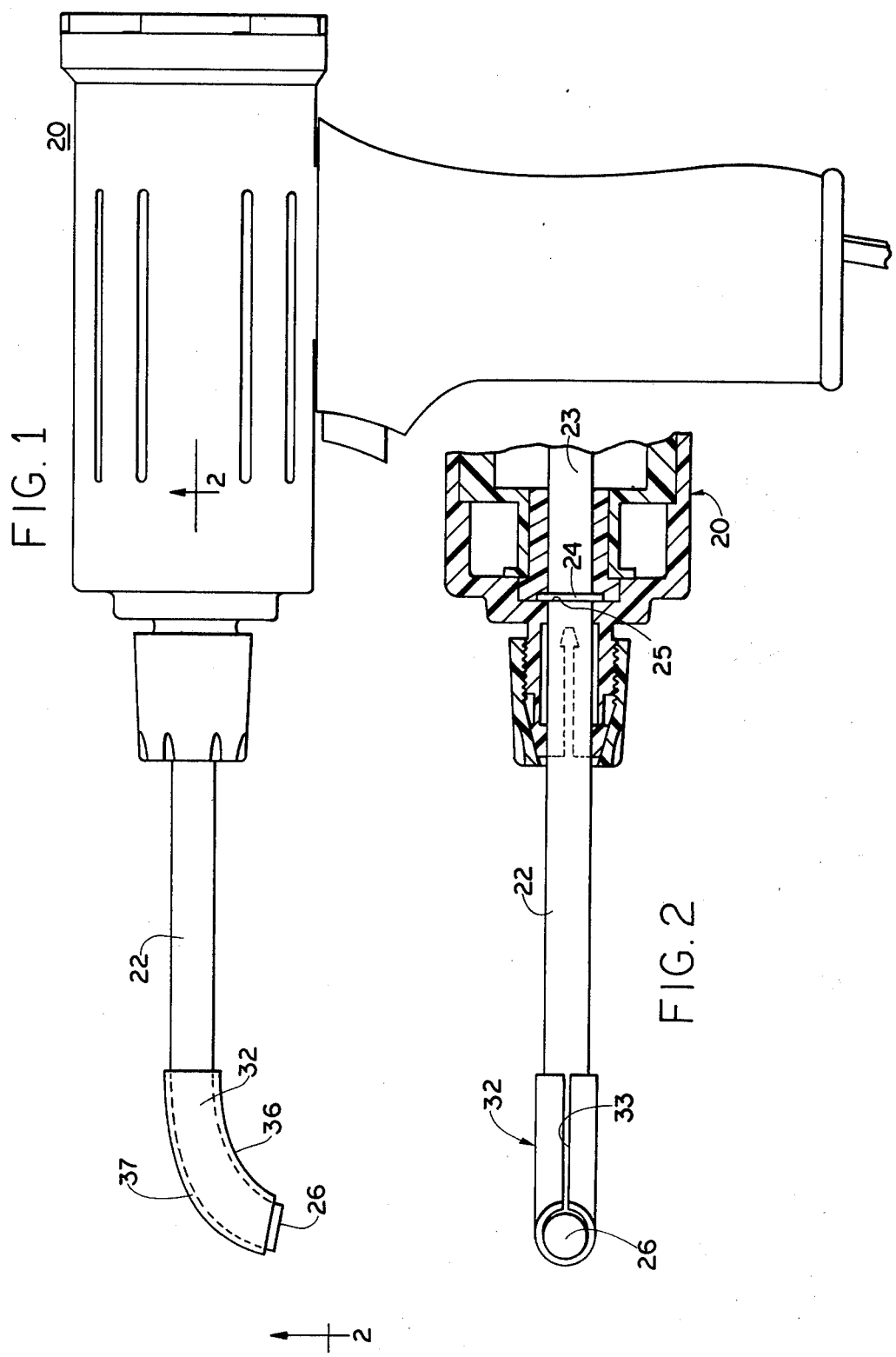

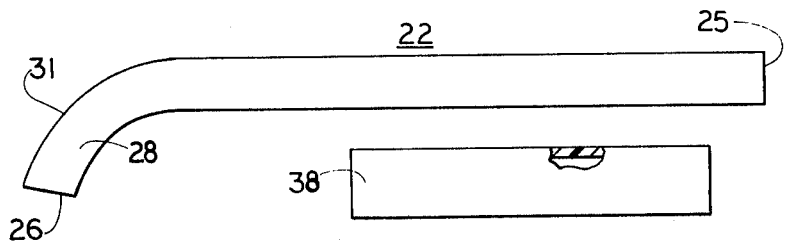
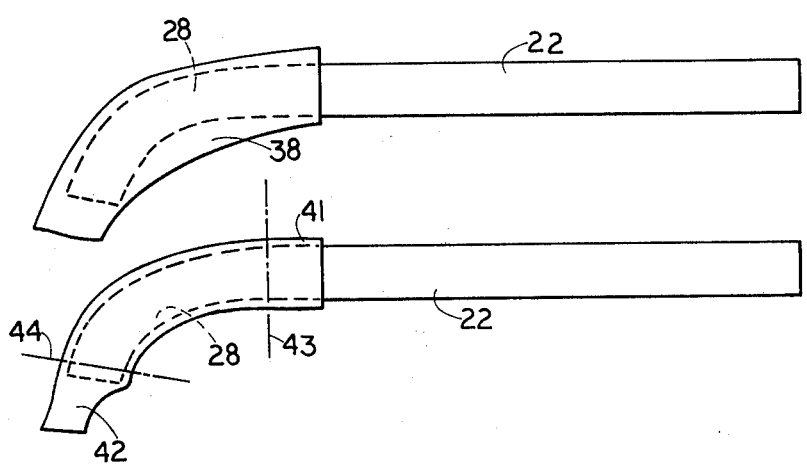
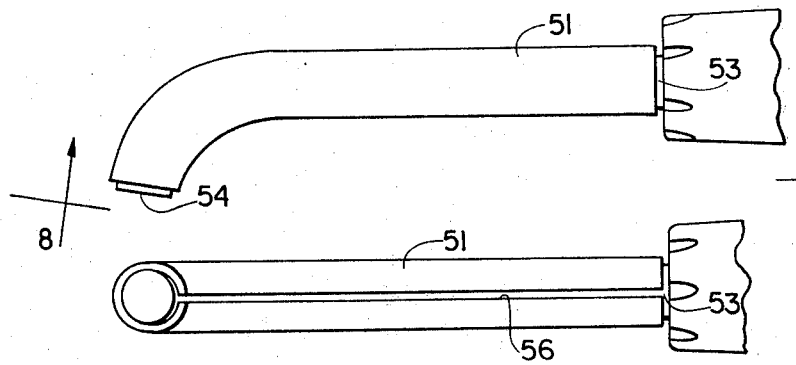

METHOD OF MAKING A SHIELD FOR A RADIATION PROJECTOR

This is a division of my copending application Ser. No. 547,049 filed Feb. 4, 1975.

This invention relates to radiation projectors. More particularly, this invention relates to a method of forming a shield for a radiation projecting rod of an ultraviolet radiation projector of the type shown in my copending application Ser. No. 318,251 filed Dec. 26, 1972, now U.S. Pat. No. 3,868,513, issued Feb. 25, 1975.

In ultraviolet radiation projectors, radiation from a generator can be directed along a quartz rod to be projected from an end of the rod in the location where the radiation is desired. Losses of radiation can occur along the walls of the rod. Such losses can be particularly serious at a bend in the rod. An object of this invention is to provide a shield for an ultraviolet radiation projecting rod which absorbs unwanted radiation which may escape through walls of the rod.

Ultraviolet radiation can be projected into a restricted location or body opening as when the projector is used in dentistry to irradiate an ultraviolet reactive resin applied to the teeth to fill cavities or to serve as a protective coating on biting surfaces of the teeth. A further object of this invention is to provide a shield which closely fits around the radiation projecting rod but which can readily be removed from the rod during sterilization of the rod and of the shield.

When a radiation shielding coating is applied to a wall of a radiation projecting rod or when a shield firmly grips the rod, there can be substantial reduction of the radiation delivered by the radiation projecting end of the rod, and a further object of this invention is to provide a shield which absorbs radiation that escapes through walls of the rod without substantially reducing the radiation delivered at the radiation projecting end of the rod.

A further object of this invention is to provide a shield for a radiation projecting rod which fits closely around the rod but with which there is an air interface between the inside of the shield and the wall of the rod.

A further object of this invention is to provide a method of forming a shield for an ultraviolet piping rod which does not substantially reduce the radiation delivered by the rod.

Briefly, this invention provides a method of forming a shield for a radiation piping rod which is formed of resin tubing which fits closely around the rod but with an air interface between the shield and walls of the rod. The shield is formed of resilient resin tubing which fits closely around the rod but with an air interface maintained between the shield and the rod. The shield can be formed from expanded shrinkable resin tubing which is substantially opaque to ultraviolet radiation. The tubing can be formed of the fluorocarbon resin commonly known as Teflon (a trademark of E. I. duPont de Nemours & Company), and can be loaded with carbon to render it opaque to ultraviolet radiation. The tubing is mounted on the portion of the rod to be shielded or on a mandrel or form rod of similar configuration, and the tubing and the rod on which the tubing is mounted are heated to relax the tubing so that the tubing shrinks upon the rod and tightly grips the rod. The tubing and the rod are permitted to cool so that the tubing becomes set in its shrunken shape. Excess tubing is cut away, and the tubing is slit lengthwise of the rod. Preferably, the lengthwise slit is made on the inside of any curvature or bend in the rod. The tubing is peeled away from the rod to form the finished shield. The resiliency of the shield causes it to fit closely around the radiation piping rod while the air interface is maintained between the radiation piping rod and the shield so that the shield does not interfere with radiation being piped along the rod but the shield can absorb radiation which is lost through the walls of the rod.

The above and other objects and features of the invention will be apparent to those skilled in the art to which this invention pertains from the following detailed description and the drawings in which:

FIG. 1 is a view in side elevation of an ultraviolet radiation projector equipped with a radiation shield constructed in accordance with an embodiment of this invention;

FIG. 2 is a view in section taken on the line 2—2 in FIG. 1;

FIG. 3 is a view in side elevation of a radiation piping rod which forms a part of the projector shown in FIG. 1;

FIG. 4 is a view in side elevation of a length of expanded shrinkable tubing from which the shield shown in FIG. 1 is formed;

FIG. 5 is a view in side elevation of the rod shown in FIG. 3 with the length of tubing shown in FIG. 4 mounted thereon prior to shrinking thereof;

FIG. 6 is a view in side elevation of the rod and of the tubing after heating to permit shrinking of the tubing, lines of cut being shown in dot-dash lines;

FIG. 7 is a fragmentary view in side elevation of an ultraviolet radiation projector equipped with a radiation shield constructed in accordance with another embodiment of this invention;

FIG. 8 is a bottom plan view looking in the direction of the arrows 8—8 in FIG. 7;

In the following detailed description and the drawings, like reference characters indicate like parts.

Figures 9, 10, 11, 12:
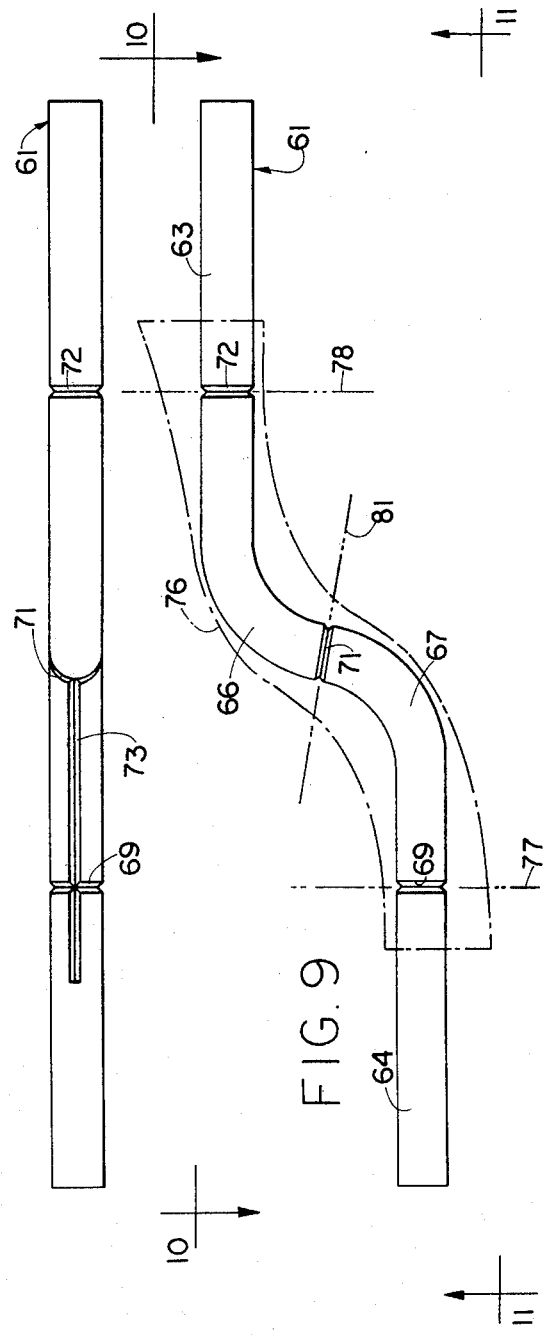
FIG. 9 is a top plan view of a mandrel for forming radiation shields in accordance with the method of this invention, a length of tubing being shown thereon in dot-dash lines, lines of cut being shown in double-dot-dash lines.
FIG. 10 is a view in side elevation of the mandrel shown in FIG. 9 looking in the direction of the arrows 10—10 in FIG. 9.
FIG. 11 is a view in side elevation of the mandrel shown in FIG. 9 looking in the direction 11—11 in FIG. 9.
FIG. 12 is an end elevational view of the mandrel shown in FIGS. 9-11 inclusive.

In FIGS. 1 and 2 is shown an ultraviolet radiation projector 20 in which ultraviolet radiation is projected along a quartz rod 22. The projector 20 includes a light collecting rod 23 (FIG. 2) along which ultraviolet radiation is directed by a radiation generator, not shown in detail, which can be of the type shown, described and claimed in my aforementioned copending application Ser. No. 318,251 (now U.S. Pat. No. 3,868,513). The radiation is directed through a filter 24, which absorbs unwanted wave lengths of radiation and into a right hand end face 25 of the rod 22 to be piped along the rod 22 to be discharged at an opposite end face 26 of the rod 22.

As shown in FIG. 3, the rod 22 includes an arcuate portion or bend 28. A major portion of the loss of radiation through walls of the rod 22 occurs at an outer face 31 of the bend 28.

Radiation which is discharged at the outer face 31 of the bend 28 is absorbed by a radiation shield 32 (FIG. 1). The shield 32 is formed of resilient resin material which is sufficiently heat resistant to permit ready sterilization thereof but which fits closely around the bend 28. Preferably, the shield 32 is formed of the polytetrafluoroethylene resin which is known as Teflon (a trademark of E. I. duPont de Nemours & Company). The resin may be filled or loaded with a material, such as carbon, which is opaque to the radiation to be absorbed. The shield is provided with a lengthwise slit 33 (FIG. 2). The slit 33 extends lengthwise of the shield 32 spaced from the portion thereof covering the outer face 31 of the bend 28 of the rod 22 and preferably extends along the inner side 36 of a bend 37 in the shield 32.

The shield 32 is formed from a length 38 (FIG. 4) of heat shrinkable polytetrafluoroethylene tubing. The length 38 is mounted on the rod 22 overlying the bend 28 as shown in FIG. 5. The rod 22 and the length of tubing 38 are heated to a sufficient temperature to permit the tubing to shrink tightly upon and against the rod at the bend 28 as shown in FIG. 6 to tightly embrace the bend portion of the rod 22. Excess portions 41 and 42 of the tubing are removed by circumferential cuts 43 and 44, respectively, to form a shrunken tubing section surrounding the bend portion of the rod. If the shrunken tubing section is permitted to remain on the rod without removal thereof, it has been found that the shrunken tubing section absorbs much of the radiation carried by the tube which would have been discharged through the end face 26 if there had been no shrunken tubing section thereon. A lengthwise cut is then formed in the shrunken tubing section to form the slit 33 (FIG. 2), and the shrunken tubing section is peeled off of the rod 22 and is replaced thereon as the completed shield 32. The removal and replacing of the tubing permits forming of an air interface between the outer wall of the rod 22 and the interior of the shield 32 with limited portions of the shield touching the rod so that the shield does not absorb any significant portion of the radiation which would be discharged from the face 26 of the rod if there were no shield in place thereof.

If desired, a shield 51 (FIGS. 7 and 8) can be formed which is similar to the shield already described but which covers substantially all of the exposed portions of a rod 53 other than a radiation delivering face 54 thereof. The shield 51 can be prepared in the manner already described, and the shield 51 is provided with a lengthwise slit 56 permitting stripping thereof from the rod 53 on which the shield 51 is formed to establish an air interface between the outer wall of the rod 53 and the interior of the shield 51.

In FIGS. 9-12 inclusive is shown a mandrel 61 for use in forming shields in accordance with the method of this invention. The mandrel 61 includes outer straight sections 63 and 64 (FIG. 9) and curved or bend portions 66 and 67, which conform to the shape of bend portions of rods on which shields are to be mounted. Circumferential grooves 69, 71 and 72 are formed in the mandrel 61. In addition, lengthwise grooves 73 (FIG. 10) and 74 (FIG. 11) are formed along inner surfaces of the bend portions 66 and 67. A length of heat shrinkable tubing 76 (FIG. 9) is mounted on the mandrel 61, and the mandrel 61 and the length of tubing 76 are heated to permit the length of tubing 76 to shrink tightly around the mandrel 61. Circumferential cuts are made in the shrunken length of tubing as indicated by double-dot-dash lines 77 and 78 to eliminate excess portions of the shrunken length of tubing. A circumferential cut is made as indicated by the double-dot-dash line 81 between the bend portions of the mandrel to divide the shrunken length of tubing into two portions. The circumferential grooves 69, 71 and 72 serve to guide a knife (not shown) to make the circumferential cuts. Lengthwise cuts are made in the tubing portions by a knife guided by the lengthwise grooves 73 and 74 in the mandrel 61, and completed shields are peeled from the mandrel 61 and can be mounted on rods in the manner already described. Since the bend portions 66 and 67 of the mandrel extend into each other without a break, there is no deforming of the shrunken tubing at meeting ends of the bend portions 66 and 67.

The shields have been described with relation to ultraviolet radiation projectors of a type used in dentistry but can be used similarly in connection with ultraviolet radiation projectors for other purposes such as those used in medical therapy and diagnosis.

The shields have been described in particular with reference to radiation piping rods for use in projecting ultraviolet radiators. However, the shields of this invention and the method of making shields can be used similarly in connection with radiation piping for use in projecting visible and infrared radiation and are particularly useful in connection with radiation piping for use with radiation of wave lengths between 10 nanometers and $10^6$ nanometers.

The shields and the method of forming shields which have been described above and illustrated in the drawings are subject to modification without departing from the spirit and scope of the appended claims.

Having described my invention, what I claim as new and desire to secure by Letters Patent is:

1. A method of forming a shield for a radiation piping rod which comprises disposing a length of heat-shrinkable, resilient plastic resin tubing on a mandrel conforming to the rod, heating the mandrel and the length of tubing to a sufficient temperature to allow the tubing to shrink around the mandrel, cooling the mandrel with the length of tubing thereon to set the resin of the tubing in its shrunken condition, forming a lengthwise slit in the length of tubing, stripping the length of tubing from the mandrel to form the shield, and mounting the shield on the rod.

2. A method as in claim 1 wherein the mandrel is the radiation piping rod and the shield is replaced on the rod after being stripped from the rod so that there is an air interface between the rod and the interior of the shield.

3. A method as in claim 1 wherein the radiation piping rod includes a bend portion, the mandrel includes two bend portions which merge into each other, a circumferential slit is formed in the length of tubing between the bend portions of the mandrel after the resin of the tubing has been set in its shrunken condition to divide the shrunken length of tubing into two portions, and lengthwise slits are formed in both portions to form two shields.

4. A method of forming a shield for a radiation piping rod which comprises forming a resilient plastic resin tube on a mandrel conforming to the rod, forming a lengthwise slit in the tube, stripping the tube from the mandrel to form the shield, and mounting the shield on the rod.

* * * * *